(12) United States Patent
Ikegami et al.

(10) Patent No.: US 8,999,131 B2
(45) Date of Patent: Apr. 7, 2015

(54) ELECTROPHORETIC MOBILITY MEASUREMENT CELL AND MEASUREMENT APPARATUS AND METHOD USING THE SAME

(71) Applicants: Mayumi Ikegami, Osaka (JP); Katsuhiro Morisawa, Osaka (JP); Tamotsu Hamao, Osaka (JP); Hidehiro Atagi, Osaka (JP)

(72) Inventors: Mayumi Ikegami, Osaka (JP); Katsuhiro Morisawa, Osaka (JP); Tamotsu Hamao, Osaka (JP); Hidehiro Atagi, Osaka (JP)

(73) Assignee: Otsuka Electronics Co., Ltd. (JP)

( * ) Notice: Subject to any disclaimer, the term of this patent is extended or adjusted under 35 U.S.C. 154(b) by 0 days.

(21) Appl. No.: 14/045,342

(22) Filed: Oct. 3, 2013

(65) Prior Publication Data
US 2014/0027286 A1    Jan. 30, 2014

Related U.S. Application Data

(63) Continuation of application No. PCT/JP2012/056444, filed on Mar. 13, 2012.

(30) Foreign Application Priority Data

Apr. 26, 2011 (JP) .................................. 2011-098624

(51) Int. Cl.
*G01N 27/447* (2006.01)
*C07K 1/26* (2006.01)

(52) U.S. Cl.
CPC ............ *G01N 27/44756* (2013.01); *C07K 1/26* (2013.01); *G01N 27/44721* (2013.01)

(58) Field of Classification Search
CPC .......... G01N 27/447; G01N 27/44756; G01N 27/44721; G01N 27/221; B01L 2400/0418; B03C 5/00; C01K 1/26
USPC .......................................... 204/450, 549, 645
See application file for complete search history.

(56) References Cited

U.S. PATENT DOCUMENTS

| | | | |
|---|---|---|---|
| 4,097,153 A | 6/1978 | DeRemigis | |
| 4,373,807 A * | 2/1983 | Gouesbet | ..................... 356/28.5 |

(Continued)

FOREIGN PATENT DOCUMENTS

| | | |
|---|---|---|
| JP | S52145291 A | 12/1977 |
| JP | H11248678 A | 9/1999 |
| JP | 2000009690 A | 1/2000 |
| JP | 2002005888 A | 1/2002 |
| JP | 2003057181 A | 2/2003 |
| JP | 2010078394 A | 4/2010 |
| WO | 2010016359 A1 | 2/2010 |

OTHER PUBLICATIONS

International Search Report Application No. PCT/JP2012/056444 Completed: Jun. 6, 2012; Mailing Date: Jun. 19, 2012 2 pages.

*Primary Examiner* — Jennifer Dieterle
(74) *Attorney, Agent, or Firm* — St. Onge Steward Johnston & Reens LLC

(57) ABSTRACT

An electrophoretic mobility measurement cell includes a container having a rectangular parallelepiped internal space for introducing a sample solution, two electrodes for applying an electric field to the internal space, tubular sample injection and extraction portions in communication with the internal space, first and second caps for covering the sample injection and extraction portions and sealing the internal space, the first cap has a first side surface contacting an inner side surface of the tubular sample injection portion, the inner side surface formed so that the cross-sectional area of the tube increases with distance from the internal space, and the area of the cross section of the first side surface decreases in the direction of insertion of the first cap. The cell and electrode portions are formed integrally, the electrode portions are made disposable together with the cell, and bubbles are unlikely to remain during injection of the sample solution.

15 Claims, 8 Drawing Sheets

(56) References Cited

U.S. PATENT DOCUMENTS

| | | |
|---|---|---|
| 4,984,829 A * | 1/1991 | Saigo et al. .................. 285/334 |
| 2002/0040851 A1 | 4/2002 | Mc.Neil-Watson et al. |
| 2003/0043374 A1 | 3/2003 | Sonehara et al. |
| 2004/0251134 A1 * | 12/2004 | Sekiwa et al. ................ 204/450 |
| 2005/0229696 A1 * | 10/2005 | Takayama .................. 73/204.26 |
| 2008/0118370 A1 * | 5/2008 | Zoulkarneev et al. .......... 417/50 |
| 2009/0071833 A1 * | 3/2009 | Gorfinkel et al. ............. 204/601 |
| 2010/0167337 A1 * | 7/2010 | Tsinberg et al. ................ 435/29 |
| 2011/0135539 A1 | 6/2011 | Sekihara et al. |
| 2011/0210002 A1 * | 9/2011 | Hsieh et al. .................. 204/549 |

* cited by examiner

ELECTROPHORETIC MOBILITY MEASUREMENT CELL AND MEASUREMENT APPARATUS AND METHOD USING THE SAME

FIELD OF THE INVENTION

The present invention relates to an electrophoretic mobility measurement cell and an electrophoretic mobility measurement method using the cell.

BACKGROUND OF THE INVENTION

An apparatus that measures the electrophoretic mobility and the ζ (zeta) potential of particles that are contained inside a sample cell container and move under the influence of an electric field is called an electrophoretic mobility measurement apparatus.

With this measurement apparatus, a liquid (sample solution), in which a dispersion of particles is suspended, is contained in a cell-type test container having transparent walls (hereinafter referred to simply as "sample cell container"), light is irradiated on the sample solution, scattered light emitted from a certain region of the sample cell container is detected by a photodetector, the velocity of the particles is calculated by analyzing the frequency components of the scattered light, and a particle velocity distribution or an electrophoretic mobility distribution of the particles is calculated.

FIG. 10 is a diagram illustrating an electroosmosis phenomenon inside a conventional sample cell container. An electroosmotic flow is a movement, due to the presence of ions, of the liquid that supports the particle dispersion. The ions are transported by the electric field. The distribution of the ions is influenced by charges present on the walls of the sample cell container.

The liquid flows in one direction at locations near the inner peripheral walls of the sample cell container and flows in the opposite returning direction at a central region of the sample cell container. This is called the electroosmotic flow $U_{osm}$.

"Up" in FIG. 10 represents the net flow of the particles dispersed and suspended in the liquid. There exist planes at each of which a peripheral flow (a flow near a cell wall that flows in one direction) of the electroosmotic flow $U_{osm}$ and a central counterflow (a flow flowing in the opposite direction at a central portion side when viewed from a cross section of the cell) contact and mingle so that the velocity of the liquid becomes zero. These planes are called "stationary planes." In an electrophoretic mobility measurement method, it is considered preferable to attempt to perform a particle velocity distribution at the position of a stationary plane (see Patent Document 1).

In injecting a sample solution into a conventional electrophoretic mobility measurement cell, an electrode is set in an opening at one side of the cell and the opening is capped. The cell is then inverted and an appropriate amount of the sample solution is injected with a pipette, etc., from an opening at the other side while inclining the cell to avoid entry of bubbles. An electrode is then inserted in the opening at the other side and the opening is capped.

On the other hand, for samples mainly in bio-related fields and pharmaceutical-related fields, disposable cells, which are discarded after measurement because of adsorption of sample and attachment of contaminants on the glass cell, are adopted.

PRIOR ART DOCUMENT(S)

Patent Document 1: Japanese Unexamined Patent Publication No. 2002-5888.
Patent Document 2: Japanese Unexamined Patent Publication No. Sho 52-145291.

SUMMARY OF THE INVENTION

Although an electrophoretic mobility measurement cell such as that described above must be sealed after injection so that the sample solution does not leak, bubbles form readily inside the cell in the process of sealing. If bubbles remain, errors arise in the measurement of the electrophoretic mobility and the ζ (zeta) potential.

Also, the cell and the electrodes are manufactured as separate parts and it takes to trouble to assemble these together. Moreover, the electrodes are removed and used repeatedly and the cell must thus be disassembled to recover the electrodes after the end of measurement.

Therefore an object of the present invention is to provide an electrophoretic mobility measurement cell, with which the cell and electrode portions are formed integrally, the electrode portions are made disposable together with the cell, and bubbles are unlikely to remain during injection of the sample solution, and provide a measurement apparatus and a measurement method using the cell.

An electrophoretic mobility measurement cell according to the present invention includes a container having a rectangular parallelepiped internal space for introducing a sample solution, at least two electrodes formed in the interior of the container and being for applying an electric field to the internal space, a tubular sample injection portion in communication with the internal space, a tubular sample extraction portion in communication with the internal space, a first cap for covering the sample injection portion and sealing the internal space, and a second cap for covering the sample extraction portion and sealing the internal space, the first cap has a first side surface contacting an inner side surface of the tubular sample injection portion when the first cap is mounted, the inner side surface of the tubular sample injection portion is formed so that the cross-sectional area of the tube increases with distance from the internal space, and the area of the cross section of the first side surface decreases gradually in the direction of insertion of the first cap.

With the present arrangement, as the first cap is pushed in, the sample solution that fills the internal space flows out from between the first side surface and the inner side surface of the sample injection portion, and formation of a pocket of air between the first cap and the water surface of the sample solution can thus be prevented. Mixing of bubbles into the sample solution is thus prevented and the formation of bubbles during sample injection can be suppressed.

The inner side surface of the tubular sample injection portion may form a fixed inclination angle with respect to a centerline of the tube in a sectional side view and the first side surface of the first cap may form the fixed inclination angle with respect to a centerline of the first cap in a sectional side view. In this case, as the first cap is pushed in, the sample solution filling the internal space flows out freely and smoothly between the first side surface and the inner side surface of the sample injection portion.

Although arrangement features in regard to the first cap were described above, the same arrangement may also be adopted in the second cap that is mounted on the sample extraction portion.

Threads may be formed between the sample injection portion and the first cap, and in this case, the fitting force can be strengthened and the formation of bubbles during sample injection can be suppressed.

Threads may be formed between the sample extraction portion and the second cap.

By forming the two electrodes inside the container so as to be integral to the container, the trouble of assembling the electrodes described in regard to the background art is eliminated and an integral electrode type cell that is fully disposable can be arranged.

An electrophoretic mobility measurement method according to the present invention is a method in which a profile of central frequencies of heterodyne spectra is measured while changing the distance from a wall of the internal space, a parabola is fitted to the profile, a stationary plane inside the internal space at which the electroosmotic flow velocity is zero is specified, and the true migration velocity, based on an applied electric field, of the particles at the stationary plane is determined.

An electrophoretic mobility measurement apparatus according to the present invention includes the electrophoretic mobility measurement cell described above, an electric field applying means applying an electric field to the electrodes of the electrophoretic mobility measurement cell, a light source, an optical path splitting means splitting the light from the light source, a focusing means focusing one of the lights, resulting from the splitting by the optical path splitting means, onto the sample solution, an automatic stage moving means for moving the focal position, a phase modulating means performing phase modulation on the other light resulting from the splitting by the optical path splitting means, a spectrum measuring means receiving an interference light of the phase-modulated reference light and scattered light emitted from the sample solution and measuring a spectrum of the interference light, and an analyzing means calculating the electrophoretic mobility of the particles based on the interference light spectrum measured by the spectrum measuring means.

With the electrophoretic mobility measurement cell according to the present invention, mixing in of bubbles and repeated use of electrodes, which were the problems of conventional disposable cells, are eliminated and the shape of the sample injection port is made a tapered shape to suppress the formation of bubbles into the cell.

The above and other advantages, features, and effects of the present invention shall be made clear by the following description of the preferred embodiment made with reference to the attached drawings.

DETAILED DESCRIPTION OF THE INVENTION

A preferred embodiment of the present invention shall now be described in detail with reference to the attached drawings.

Figure 1:
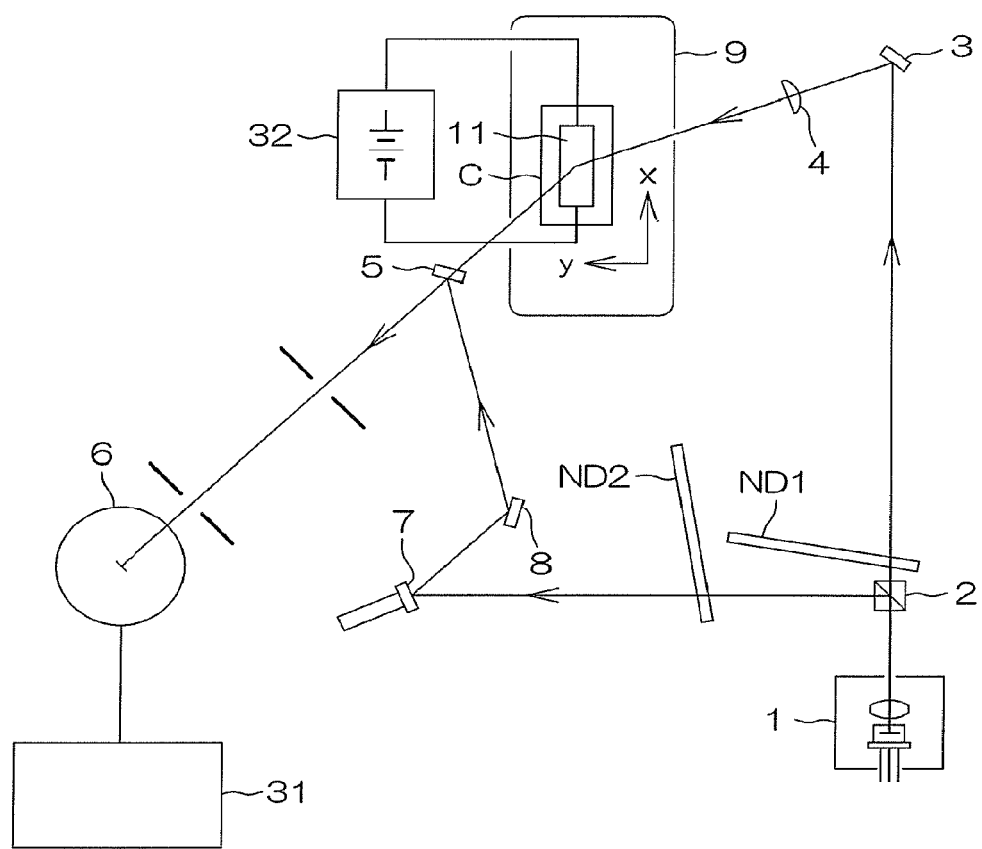
FIG. 1 is a plan view of an electrophoretic mobility measurement apparatus for measuring electrophoretic mobility by the present invention.

FIG. 1 is a plan view of an electrophoretic mobility measurement apparatus for measuring electrophoretic mobility by the present invention. The measurement apparatus includes a transparent sample cell container C, a DC power supply 32 applying an electric field to the sample cell container C, a light emitting source 1 for irradiating light onto a sample solution, which is confined in a rectangular parallelepiped internal space (chamber) 11 formed in the interior of the sample cell container C and in which sample particles are dispersed, a photodetector 6 for detecting scattered light emitted from an irradiated point of the sample solution, a modulator 7 for imparting a Doppler shift based on a branched light among the light irradiated from the light emitting source 1, and a movable stage 9 for moving the sample cell container C in any direction within an x-y plane (horizontal plane) and in a z-direction perpendicular to the x-y plane.

For example, a laser diode is used as the light emitting source 1 of the electrophoretic mobility measurement apparatus. The light of the laser diode is made incident on a half-mirror 2 and split into two lights by the half-mirror 2. One light (hereinafter referred to as the "sample light") among the lights resulting from the splitting is reflected by a mirror 3, focused by a lens 4, and made incident on the sample solution inside the internal space 11 of the sample cell container C. Scattered light from the sample solution passes through a half-mirror 5 and is detected by the photodetector 6. For example, a photomultiplier is used as the photodetector 6. The movable stage 9 includes a moving mechanism that moves the sample cell container C and is capable of automatically moving the focal point of the laser light to a measurement point, input in advance, of the sample solution in the sample cell container C.

The other light resulting from the splitting by the half-mirror 2 is referred as the "reference light." The reference light is reflected by a mirror 7, further reflected by a mirror 8, and then reflected by the half-mirror 5. The reference light reflected by the half-mirror 5 and the sample light transmitted through the half-mirror 5 propagate in the same direction and are thereby synthesized (referred to as the "interference light") and thereafter detected by the photodetector 6.

A vibrating element that vibrates the mirror 7 to apply modulation to the reference light is mounted on the mirror 7. By the vibration of the vibrating element, the mirror 7 is made to vibrate sinusoidally at a predetermined amplitude and frequency. The vibrating element may, for example, be arranged from a piezoelectric transducer (PZT).

The interference light of the reference light and the scattered light made incident on the half-mirror 5 is made incident on the photodetector 6 and from an output signal of the photodetector 6, a power spectrum of the interference intensity of the light is detected by a spectrum analyzer 31. This spectrum is referred to as the "heterodyne spectrum."

By observing the waveform (peak frequency, half-width, etc.) of the heterodyne spectrum, the electrophoretic mobility of the sample particles can be measured.

Figure 2:
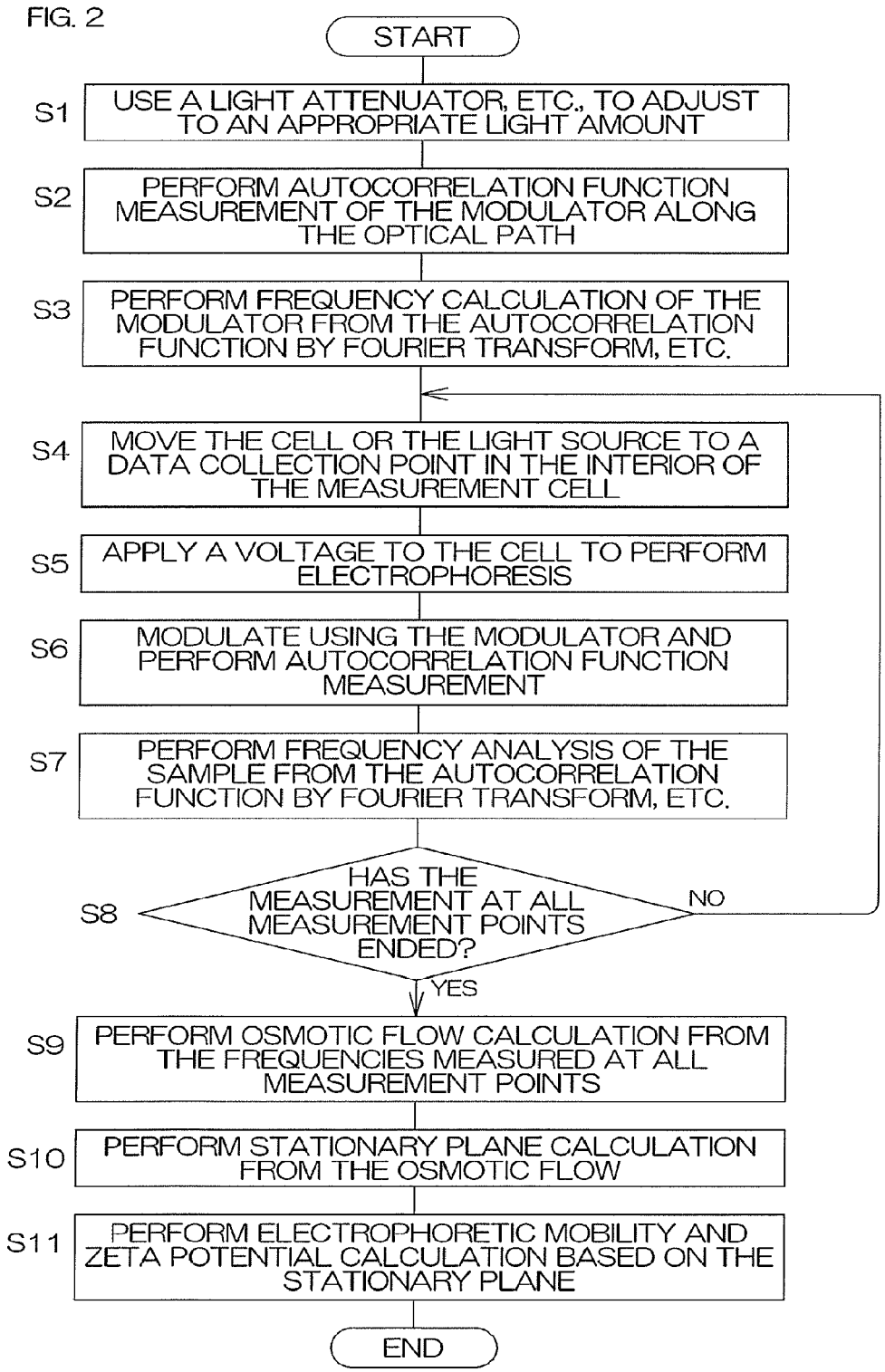
FIG. 2 is a flowchart for describing a procedure for calculating the electrophoretic mobility.

A procedure for calculating the electrophoretic mobility shall now be described using a flowchart (FIG. 2). First, the sample solution, in which the sample particles are dispersed, is injected into the internal space 11 of the sample cell container C, and in a state where an electric field is not applied, the light amount of the laser diode is adjusted to a light amount appropriate for measurement by using light attenuators ND1 and ND2, etc., that are inserted between the half-mirror 2 and the mirrors 3 and 7 (step S1). Vibration is then applied to the vibrating element and measurement of the light intensity (function of time) received by the photodetector 6 is performed (step S2). The measured light intensity expresses an "autocorrelation function" of the scattered light. The autocorrelation function is subject to Fourier transform analysis by the spectrum analyzer 31 to calculate and record the heterodyne spectrum (step S3).

Then using the movable stage 9, the focal point of the sample light in the sample solution is moved and stopped at a predetermined position. As shall be described later using FIG. 3 and FIG. 4, several points in the z-direction from an upper wall to a lower wall of the internal space 11 formed inside the sample cell container C are set as stop positions, and from among these several points, a single point (the z-coordinate of which shall be z1) at which measurement is to be made first is selected and the focal point is stopped at that position (step S4).

A predetermined DC field is then applied to the internal space 11 using the DC power supply 32 to make the sample particles electrophorese (step S5). The vibrating element is then vibrated to measure the autocorrelation function (step S6) and the heterodyne spectrum is measured and recorded by the spectrum analyzer 31 (step S7). In comparison to the heterodyne spectrum calculated in step S3, the present heterodyne spectrum is shifted in central frequency due to the osmotic flow generated by the movement of the sample particles. This shift Δf can be measured.

Thereafter, the measurement point is changed (z1→z2) and the procedure of steps S5 to 7 is repeated (step S8). When measurements are ended for all measurement points (for example, z1 to z5) that were set in advance, a set of heterodyne spectra can be plotted with the z-coordinate of the measurement point as the ordinate and the frequency as the abscissa as shown in FIG. 3 and FIG. 4.

Figure 3:
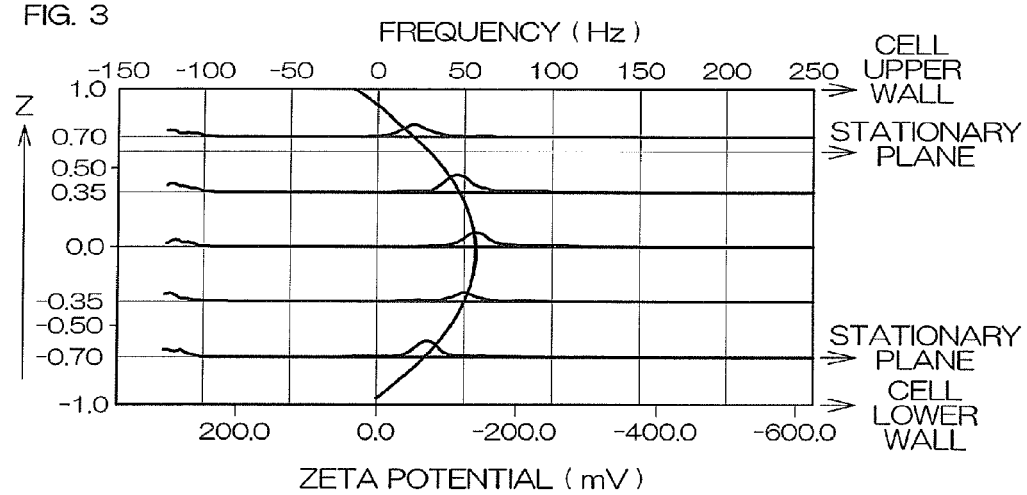
FIG. 3 is a graph with a z-coordinate of a measurement point as the ordinate and frequency as the abscissa and in which a set of heterodyne spectra of interference light is plotted.
Figure 4:
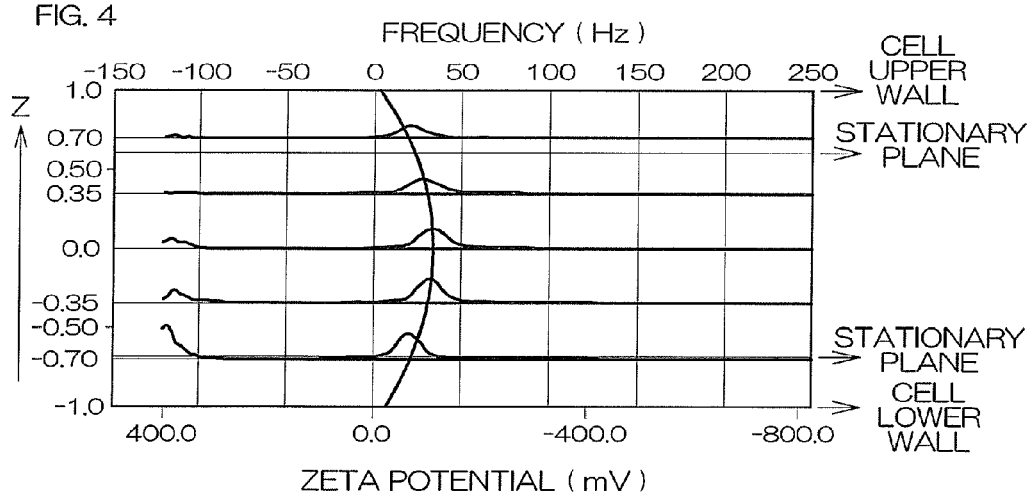
FIG. 4 is a graph with the z-coordinate of a measurement point as the ordinate and the frequency as the abscissa and in which a set of heterodyne spectra is plotted.

The frequency represented by the abscissa of each of the graphs of FIG. 3 and FIG. 4 corresponds to an apparent migration velocity of the sample particles. The apparent migration velocity is a sum of the true migration velocity of the sample particles based on the electric field and the electroosmotic flow velocity, and the electroosmotic flow velocity differs according to the z-coordinate of the measurement point as shall be described below. Therefore, by analyzing the velocity profile of the electroosmotic flow that differs according to the z-coordinate, a stationary plane at which the electroosmotic flow velocity is zero can be specified and the true migration velocity of the sample particles at the stationary plane can be determined.

Here, to describe the electroosmotic flow, the wall surfaces of the internal space inside the sample cell container are negatively charged. Positively charged ions and particles thus gather near the wall surfaces and when an electric field parallel to the wall surfaces is applied, a flow toward the negative electrode side occurs near the wall surfaces due to these ions and to compensate for this flow, a flow in the opposite direction occurs at a central portion of the internal space. This flow is the electroosmotic flow and there exists a plane that is located at a certain distance from a wall surface of the internal space and is a plane at which the electroosmotic flow velocity is zero. This plane is the stationary plane and the migration velocity of the sample particles at this stationary plane expresses the true migration velocity of the sample particles based on the electric field.

Based on a profile of the electroosmotic flow velocities that differ according to the z-coordinate, the z-coordinate of the stationary plane at which the electroosmotic flow velocity is zero is determined by the following calculation.

The following formula (1) holds because the apparent migration velocity is the sum of the true migration velocity of the sample particles based on the electric field and the electroosmotic flow velocity.

$$U_{obs}(z)=U_p+U_{osm}(z) \qquad (1)$$

z: distance from the center of the internal space $U_{obs}(z)$: apparent migration velocity measured at the position z $U_p$: true migration velocity of the particles $U_{osm}(z)$: electroosmotic velocity at the position (z)

In a rectangular parallelepiped internal space, the apparent migration velocity $U_{obs}(z)$ can be approximated by the following second-order formula (2) regarding z.

$$U_{obs}(Z)=AU_0(z/b)^2+\Delta U_0(z/b)+(1-A)U_0+U_p \qquad (2)$$

Here, the coefficient A is expressed by $$A=1/[(2/3)-(0.420166/k)] \qquad (3)$$

and k is a ratio of lengths a and b of respective sides of a cross section of the internal space perpendicular to the migration direction, that is, k=a/b (a>b). $U_0$ is an average value of flow velocities of the solution at the upper and lower wall surfaces and $\Delta U_0$ is a difference of the flow velocities of the solution at the upper and lower wall surfaces of the cell.

The stationary plane is located at the position at which $U_{obs}=U_p$, and the migration velocity observed at the stationary plane is the true migration velocity of the particles. The true migration velocity $U_p$ of the particles can be determined by measuring apparent migration velocities $U_{obs}(z)$ at various positions by moving the measurement point vertically, fitting a parabola by a least squares method based on the data, and performing coefficient comparison.

FIG. 3 and FIG. 4 are graphs in which actually measured sets of heterodyne spectra are plotted. In regard to the ordinate, the z-coordinate of the upper wall of the internal space is expressed as "1," the z-coordinate of the lower wall of the internal space is expressed as "−1," and the z-coordinate of the middle position between the upper wall and the lower wall of the internal space is expressed as "0." The abscissa represents the frequency of the heterodyne spectra and the central frequency of a heterodyne spectrum measured in the state where an electric field is not applied to the sample cell container C is expressed as 0 [Hz].

FIG. 3 is a graph for the case where the sample solution is prepared by mixing a polystyrene latex of 262 nm diameter (concentration: 0.001%) in a 10 mM (millimolar) sodium chloride aqueous solution. The measurement conditions are refractive index of solution: 1.3328; viscosity of solution: 0.8878; and dielectric constant of solution: 78.3.

FIG. 4 is a graph for the case where the sample solution is prepared by mixing a polystyrene latex of 262 nm diameter (concentration: 0.001%) in a 100 mM (millimolar) sodium chloride aqueous solution. The measurement conditions are refractive index of solution: 1.3328; viscosity of solution: 0.8878; and dielectric constant of solution: 78.3.

In FIG. 3, the electric field strength is −10.64[V/cm]. In FIG. 4, the electric field strength is −8.04[V/cm]. In both FIG. 3 and FIG. 4, the profile of the central frequencies of the heterodyne spectra is substantially a second-order curve (parabola).

A parabola was fitted to each profile by the least squares method and a comparison was made with the coefficients of formula (2). As a result, in the case of FIG. 3, the plane at z=0.6017 and the plane at z=−0.6936 were found to be the stationary planes. The migration velocity of the sample particles at the stationary plane was determined and based on the migration velocity, the electrophoretic mobility was determined to be $-5.643 \times 10^{-4}$ [cm$^2$/Vs] and the $\zeta$ potential of the particles was determined to be −72.36 mV.

In the case of FIG. 4, the plane at z=0.6078 and the plane at z=−0.6867 were found to be the stationary planes. The migration velocity of the sample particles at the stationary plane was determined and based on the migration velocity, the electrophoretic mobility was determined to be $-5.335 \times 10^{-4}$ [cm$^2$/Vs] and the $\zeta$ potential of the particles was determined to be −68.41 mV.

The true migration velocity based on the applied electric field of the particles at the stationary plane can thus be determined under the premise of the internal space being a rectangular parallelepiped by measuring the profile of the central frequencies of heterodyne spectra while changing the distance from a wall, fitting a parabola to the profile, and using the formula (2) to specify the stationary plane at which the electroosmotic velocity is zero. Also, the stationary plane can be determined from the electroosmotic flow measurement using the automatic stage moving function of the movable stage 9 to realize accurate measurement of the electrophoretic mobility.

The structure of the sample cell container C related to the present invention is shown in FIG. 5A to FIG. 5C, FIG. 6, and FIG. 7. The direction of electric field application is indicated by x and the direction perpendicular thereto is indicated by y. A horizontal plane is defined by x-y. The direction of the laser beam is parallel to the y-direction. The z-direction is a direction perpendicular to x and y. The movable stage 9 is operated so that the sample cell container C moves along the z-direction.

The sample cell container C is shaped from a transparent resin of rectangular parallelepiped shape. For example, polystyrene may be adopted as the transparent resin. In the interior of the rectangular parallelepiped (referred to as the "sample cell container main body 10") is formed the sealed space (internal space) 11 that is to be filled with the sample solution. As with the outer shape of the sample cell container main body 10, the shape of the internal space 11 is also a rectangular parallelepiped. A side surface 12 perpendicular to the y-direction of the sample cell container main body 10 shown in FIG. 5A and a side surface 13 perpendicular to the y-direction of the internal space 11 are the surfaces at which the laser beam enters and exits and these surfaces are mirror-finished especially carefully. A pair of embedded electrodes 14, which are for generating an electric field and are embedded in and thereby made integral to the sample cell container main body 10, are disposed in states of being exposed in the internal space 11 at respective ends in the x-direction of the sample cell container main body 10. Each embedded electrode 14 is made of gold-plated copper or brass and as is clear from FIG. 5B, which is a front sectional view, has a U-shaped cross section and is embedded in the sample cell container main body 10.

To give an example of dimensions, the size of the internal space 11 as viewed in a y-z cross section is 1×5 mm and the distance between electrodes is 24 mm. The calculated spatial volume is 120 to 130 μliters. A conventional electrophoretic mobility measurement cell is large in cell size (for example, 2×10 mm) and requires a certain sample volume because the sample injection is performed with a syringe, etc. However, for samples mainly in bio-related fields and pharmaceutical-related fields (samples of a high degree of hazard or a microquantity or precious sample), etc., the less the sample amount necessary, the more preferable. Therefore by making small the size of the sample cell container C and the distance between electrodes, it becomes possible to realize a minimum volume for a fully disposable cell.

An injection port 15 and an extraction port 16 for the sample solution are formed at upper surfaces of the respective ends in the x-direction of the sample cell container main body 10, a cylindrical tubular injection portion 17 is erected so as to surround the injection port 15, and a cylindrical tubular extraction portion 18 is erected so as to surround the ejection port 16. An inner side surface 17a of the injection portion 17 and an inner side surface 18a of the extraction portion 18 are respectively formed to tubular shapes and are in communication with the internal space 11. Both the injection portion 17 and the extraction portion 18 are formed of the same transparent resin as the sample cell container main body 10.

The inner side surface 17a of the injection portion 17 is formed to be inclined so that the cross-sectional area of the tube increases with distance from the sample cell container main body 10. The inner side surface 18a of the extraction portion 18 is also formed to be inclined so that the cross-sectional area of the tube increases with distance from the sample cell container main body 10.

A cap 21 that covers and seals the internal space is provided to prevent leakage of the sample solution from the injection portion 17 after the internal space 11 has been filled with the sample solution, and a cap 22 that covers and seals the internal space is provided to prevent leakage of the sample solution from the extraction portion 18. If the shapes of the injection portion 17 and the extraction portion 18 are the same, the shapes of the caps 21 and 22 are the same as well. It is convenient to make the caps the same in shape because this eliminates the need to manage the caps according to injection and extraction.

In the following description, it shall be deemed that the shapes of the injection portion 17 and the extraction portion 18 are the same and the shapes of the caps 21 and 22 are the same, and only the shapes of the injection portion 17 and the cap 21 shall be described.

Figure 6:
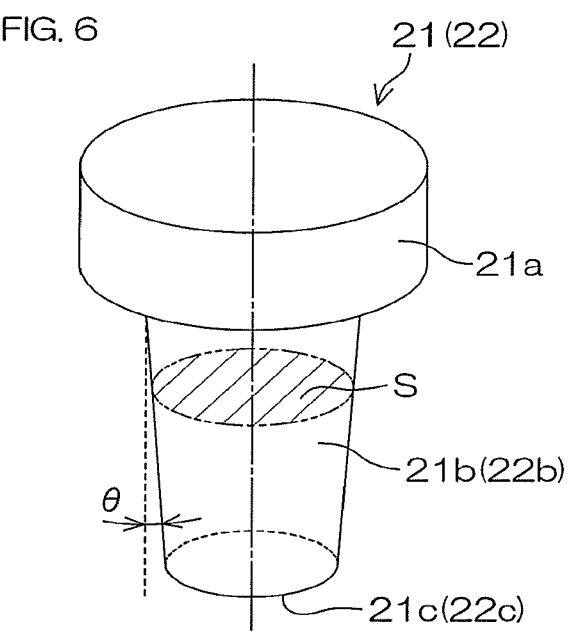
FIG. 6 is a perspective view of a shape of a cap that covers an injection portion or an extraction portion.

FIG. 6 is a perspective view of the shape of the cap 21 that covers the injection portion 17. The cap 21 is formed of a resin, such as polytetrafluoroethylene, etc., and is arranged from a knob portion 21a for holding with a hand, a side surface portion 21b contacting the inner side surface 17a of the cylindrical tube of the injection portion 17 or the inner side surface 18a of the cylindrical tube of the extraction portion 18, and a bottom surface portion 21c. A hypothetical cross section of the side surface portion 21b resulting from sectioning perpendicularly along a centerline of the cap 21 is indicated by "S." The cap 21 is formed so that the area of the cross section S decreases gradually along a direction of insertion from the knob portion 21a to the bottom surface portion 21c. On the other hand, the inner side surface 17a of the injection portion 17 is formed so as to increase in cross-sectional area with distance from the injection port 15.

Specifically, the side surface portion 21b of the cap 21 is tapered in a sectional side view. An angle of inclination formed by the side surface 21b and the centerline is represented by "θ." The inner side surface 17a of the injection portion 17 is also inclined at a fixed inclination angle with respect to the centerline in a sectional side view. This "fixed inclination angle" is also equal to the angle θ of the side surface portion 21b of the cap 21.

Figure 7:
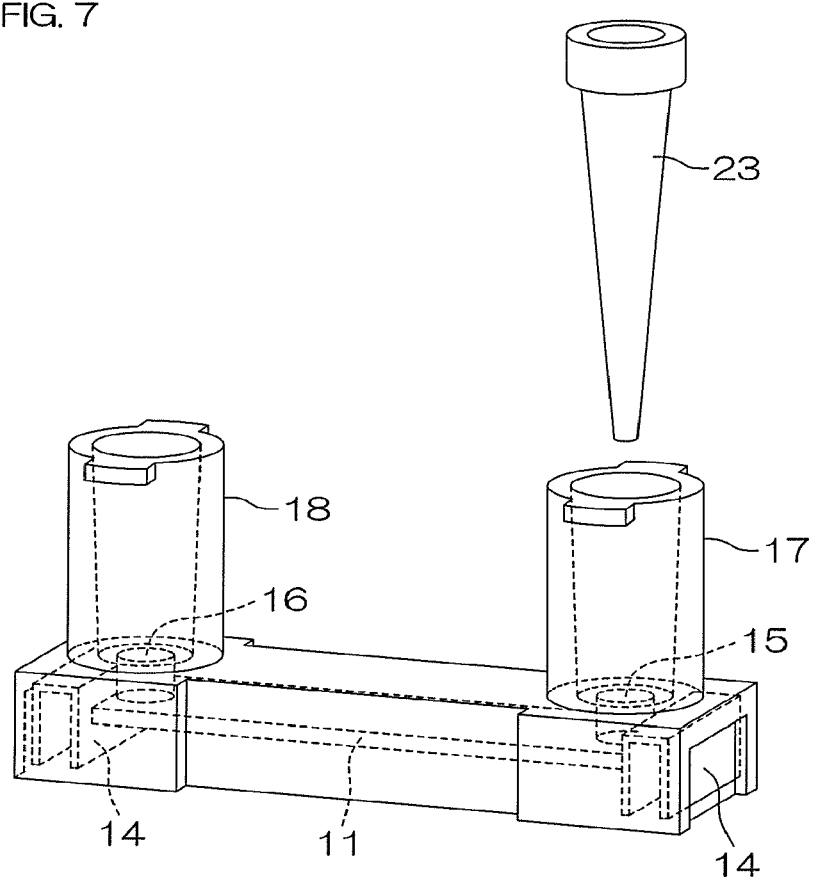
FIG. 7 is a perspective view of a micropipette and the sample cell container for describing a method of using the sample cell container.

A method of using the sample cell container C shall now be described using FIG. 7. In a state where the caps 21 and 22 are removed, a predetermined amount of the sample solution is injected from the injection portion 17 using a micropipette 23. The predetermined amount is marked on the micropipette 23 and by injecting the predetermined amount, a state is reached where the internal space 11 is filled with the sample solution and portions of the interiors of the cylindrical tubes of the injection portion 17 and the extraction portion 18 are also filled with the sample solution.

When a large amount of the sample solution that exceeds the predetermined amount is placed in the micropipette 23, the sample solution overflows from the injection portion 17 or the extraction portion 18 or a state close thereto is reached and the sample solution is wastefully lost when the caps 21 and 22 are mounted. Therefore by adhering to the predetermined amount of the micropipette 23, sample injection of a fixed amount is made possible and wasting of the injected sample amount can be eliminated.

As the caps 21 and 22 are pushed in, excess solution overflows from the injection portion 17 and the extraction portion 18 because the side surface portion 21b of the cap 21 is tapered at the angle equal to the inclination angle of the inner side surface 17a of the cylindrical tube of the injection portion 17 and the side surface portion 22b of the cap 22 is tapered at the angle equal to the inclination angle of the inner side surface 18a of the cylindrical tube of the extraction portion 18.

If the side surface portion 21b of the cap 21 is not tapered, that is, if the cap 21 is formed so that the area of the cross section S of the side surface portion 21b of the cap 21 is uniform from the knob portion 21a toward the bottom surface portion 21c and the inner side surface 17a of the cylindrical tube of the injection portion 17 is also formed to be uniform in cross-sectional area, air becomes retained between the bottom surface portion 21c of the cap 21 and the water surface of the sample solution as the cap 21 is pushed into the injection portion 17. The same applies when the cap 22 is pushed into the injection portion 18. The retained air is entrained in the sample solution as the pressure of the sample solution in the internal space 11 increases and bubbles are thereby formed readily. Once bubbles form, the bubbles become attached to the inner wall surfaces of the internal space 11 and become difficult to remove.

With the preferred embodiment of the present invention, by making the side surface portion 21b of the cap 21 and the inner side surface 17a of the cylindrical tube of the injection portion 17 be inclined at equal angles, the retention of air between the bottom surface portion 21c and the water surface of the sample solution during the mounting of the cap 21 can be prevented. Similarly, the retention of air between the bottom surface portion 22c and the water surface of the sample solution during the mounting of the cap 22 can be prevented. Bubbles are thus prevented from becoming mixed in the sample solution and forming of bubbles during sample injection can be suppressed.

An embodiment is also possible where the cap 21 is arranged to be used exclusively for the injection port, the cap 22 is arranged to be used exclusively for the extraction port, the side surface portion of one of the caps is tapered, the side surface portion of the injection port or the extraction port on which that cap is mounted is also taped, the side surface portion of the other cap is not tapered, and the side surface portion of the injection port or the extraction port on which that cap is mounted is also not taped. With this arrangement, the forming of bubbles can be prevented completely at least at the cap that is tapered and the injection port or extraction port on which the tapered cap is mounted.

Figure 8:
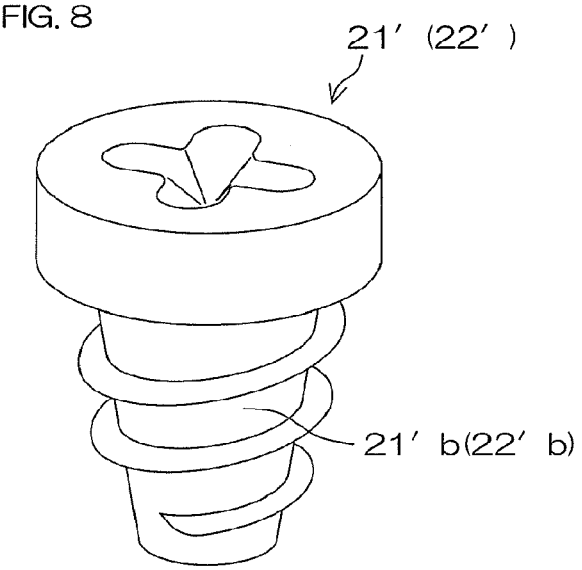
FIG. 8 is a perspective view of a cap that is tapered at a side surface portion and has a thread groove (male thread) formed thereon.

Also as shown in FIG. 8, an embodiment is possible where a side surface portion 21'b or a side surface portion 22'b of a cap 21' or 22' is tapered and has a thread groove (male groove) formed thereon, an inclined thread groove (female thread) is formed on the inner side surface of the injection portion or the inner side surface of the extraction portion on which the cap is mounted, and the cap is pushed in while turning. In this case, excess solution overflows from the injection port 19 or the extraction port 20 as the cap 21' or 22' is screwed in. By using the threaded fitting, firm coupling of the cap 21' or 22' with the injection portion or the extraction portion can be realized.

Figure 5A:
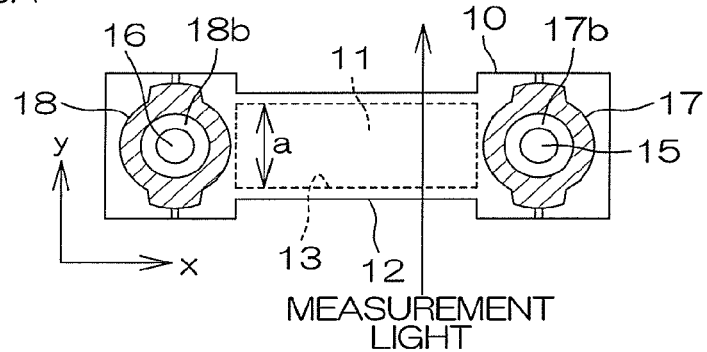
FIG. 5A is a plan view of a structure of a sample cell container.
Figure 5B:
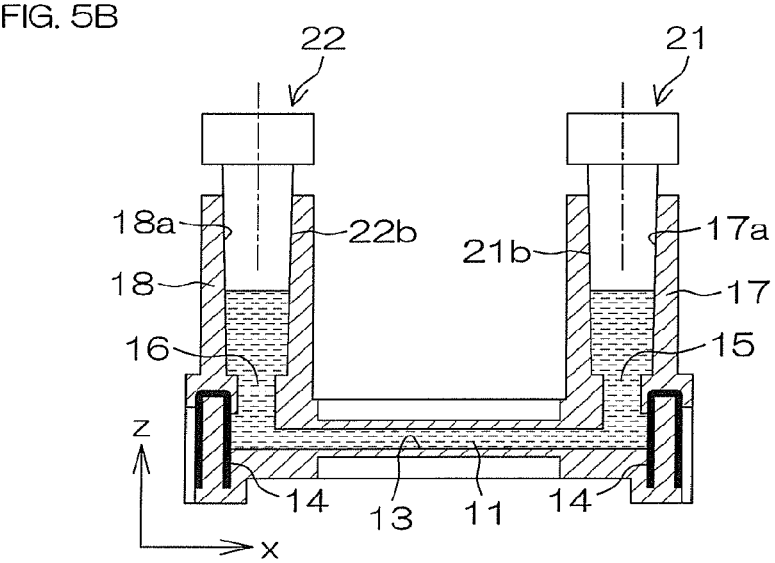
FIG. 5B is a sectional front view of the structure of the sample cell container.
Figure 5C:
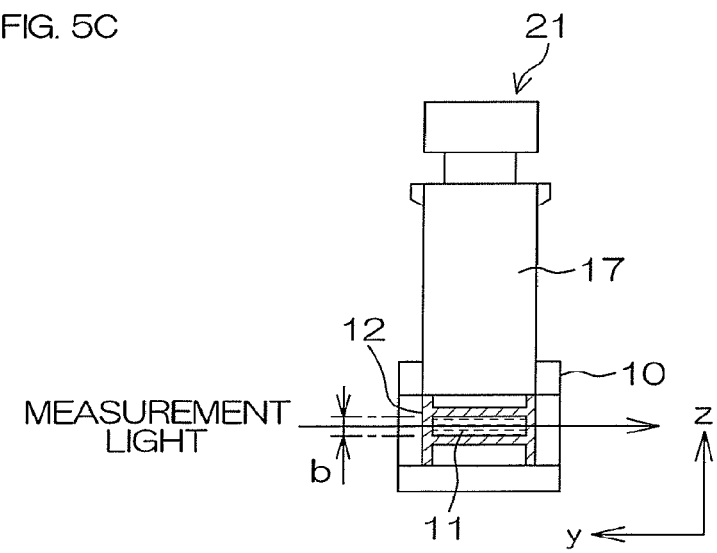
FIG. 5C is a side view (C) of the structure of the sample cell container.
Figure 9:
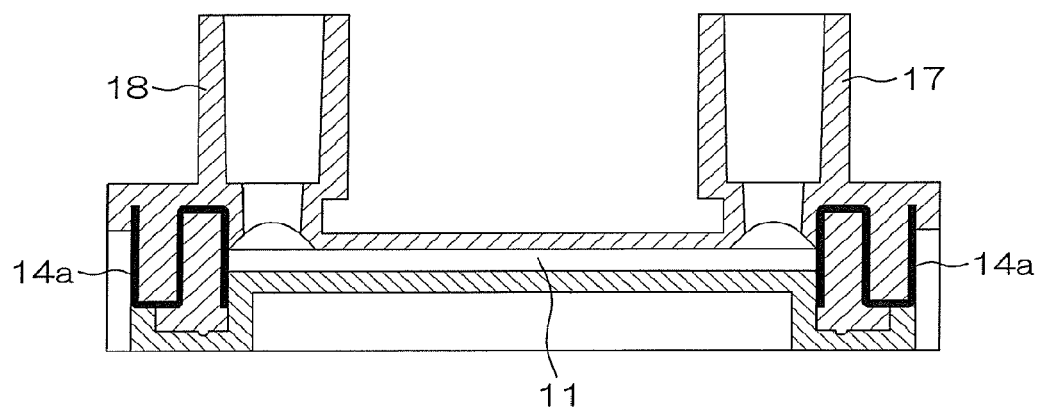
FIG. 9 is a sectional view of a modified shape of an electrode.
Figure 10:
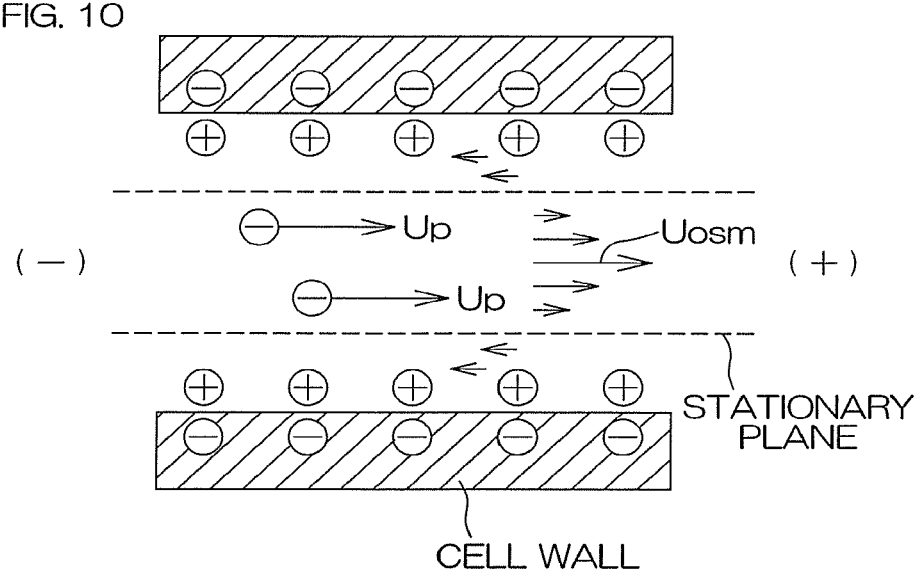
FIG. 10 is a diagram of an electroosmosis phenomenon inside a conventional sample cell container.

Although preferred embodiments of the present invention have been described above, embodiments of the present invention are not restricted to those described above. For example, the shape of the embedded electrode 14 is not restricted to that of U-shaped cross section as shown in FIG. 5B and any shape, such as an "S"-shaped cross section, an "I"-shaped cross section, etc., may be adopted. FIG. 9 shows the shape of an embedded electrode 14a arranged to have an "S"-shaped cross section by bending a metal plate twice. Besides the above, various modifications may be applied within the scope of the present invention.

What is claimed is:

1. An electrophoretic mobility measurement cell comprising: a container having a rectangular parallelepiped internal space for introducing a sample solution; at least two electrodes formed in the interior of the container and configured to apply an electric field to the internal space; a tubular sample injection portion in communication with the internal space; a tubular sample extraction portion in communication with the internal space; a first cap for covering the sample injection portion and sealing the internal space; and a second cap for covering the sample extraction portion and sealing the internal space; and
   wherein the at least two electrodes are U-shaped or S-shaped,
   wherein the first cap has a first side surface that contacts an inner side surface of the tubular sample injection portion when the first cap is mounted, and
   wherein the inner side surface of the tubular sample injection portion is formed so that an inner cross-sectional area of the tubular sample injection portion increases with distance apart from the internal space, and an area of a cross section of the first side surface decreases gradually in the direction of insertion of the first cap.

2. The electrophoretic mobility measurement cell according to claim 1, wherein the electrodes are formed integral to the container.

3. The electrophoretic mobility measurement cell according to claim 1, wherein the inner side surface of the tubular sample injection portion forms a fixed inclination angle with respect to a centerline of the tube in a sectional side view and the first side surface of the first cap forms the inclination angle with respect to a centerline of the first cap in a sectional side view.

4. The electrophoretic mobility measurement cell according to claim 1, wherein an inner side surface of the tubular sample extraction portion is formed so that an inner cross-sectional area of the tubular sample extraction portion increases with distance from the internal space, and the second cap has a second side surface contacting the inner side surface of the tubular sample extraction portion and an area of a cross section of the second side surface decreases gradually in the direction of insertion of the second cap.

5. The electrophoretic mobility measurement cell according to claim 4, wherein the inner side surface of the tubular sample extraction portion forms a fixed inclination angle with respect to a centerline of the tube in a sectional side view and the second side surface of the second cap forms the inclination angle with respect to a centerline of the second cap in a sectional side view.

6. The electrophoretic mobility measurement cell according to claim 1, wherein a female thread is formed on the inner side surface of the tubular sample injection portion and a male thread, fitting to the female thread, is formed on the first side surface of the first cap.

7. The electrophoretic mobility measurement cell according to claim 4, wherein a female thread is formed on the inner side surface of the tubular sample extraction portion and a male thread, fitting to the female thread, is formed on the second side surface of the second cap.

8. An electrophoretic mobility measurement method comprising:
preparing the electrophoretic mobility measurement cell according to claim 1;
measuring a profile of central frequencies of heterodyne spectra while changing the distance from a wall of the internal space;
fitting a parabola to the profile;
specifying a stationary plane inside the internal space at which an electroosmotic flow velocity is zero; and
determining the true migration velocity, based on an applied electric field, of the particles at the stationary plane.

9. The electrophoretic mobility measurement method according to claim 8, wherein an electrophoretic mobility measurement cell is set on a movable stage and by an automatic stage moving function of the movable stage, the stationary plane is determined from the electroosmotic flow measurement to realize accurate measurement of the electrophoretic mobility.

10. An apparatus for measuring the electrophoretic mobility of particles in a sample solution, comprising:
the electrophoretic mobility measurement cell according to claim 1; a DC power supply applying an electric field to the electrodes of the electrophoretic mobility measurement cell; a light source; a half-mirror splitting light from the light source; a lens focusing one of the lights split by the half-mirror onto the sample solution; a movable stage for moving a focal position; a vibrating element performing phase modulation on another one of the lights split by the half-mirror; a photodetector receiving an interference light of the phase-modulated reference light and scattered light emitted from the sample solution for measuring a spectrum of the interference light; and a spectrum analyzer calculating the electrophoretic mobility of the particles based on the interference light spectrum measured by the photodetector.

11. The electrophoretic mobility measurement cell according to claim 1, wherein each of said tubular sample injection portion and said tubular sample extraction portion extends from a top surface of said container.

12. The electrophoretic mobility measurement cell according to claim 11, wherein each of said tubular sample injection portion and said tubular sample extraction portion is substantially perpendicular to the top surface of said container.

13. The electrophoretic mobility measurement cell according to claim 1, wherein said at least two electrodes are U-shaped.

14. The electrophoretic mobility measurement cell according to claim 1, wherein said at least two electrodes are S-shaped.

15. The electrophoretic mobility measurement cell according to claim 1, wherein each of said container, said tubular sample injection portion, and said tubular sample extraction portion are comprised of a transparent resin.

* * * * *